United States Patent [19]

Sivik

[11] Patent Number: 5,559,261

[45] Date of Patent: * Sep. 24, 1996

[54] METHOD FOR MANUFACTURING COBALT CATALYSTS

[75] Inventor: Mark R. Sivik, Fairfield, Ohio

[73] Assignee: The Procter & Gamble Company, Cincinnati, Ohio

[*] Notice: The portion of the term of this patent subsequent to Jul. 27, 2015, has been disclaimed.

[21] Appl. No.: 508,195

[22] Filed: Jul. 27, 1995

[51] Int. Cl.$^6$ ................................................ C07F 15/06
[52] U.S. Cl. ................................................ 56/148; 556/74
[58] Field of Search ........................... 556/148, 74

[56] References Cited

U.S. PATENT DOCUMENTS

| | | | |
|---|---|---|---|
| 4,218,377 | 8/1980 | Stockinger et al. | 556/148 X |
| 4,325,884 | 4/1982 | Kang | 556/148 |
| 4,364,871 | 12/1982 | Svatek et al. | 556/148 |
| 4,425,278 | 1/1984 | Wirth et al. | 554/74 |
| 4,430,243 | 2/1984 | Bragg | 252/91 |
| 4,810,410 | 3/1989 | Diakun et al. | 252/102 |
| 4,915,854 | 4/1990 | Mao et al. | 252/8.8 |
| 5,089,162 | 2/1992 | Rapisarda et al. | 252/102 |
| 5,114,611 | 5/1992 | Van Kralingen et al. | 252/186.33 |
| 5,173,207 | 12/1992 | Drapier et al. | 252/99 |
| 5,244,594 | 9/1993 | Favre et al. | 252/186.33 |
| 5,246,612 | 9/1993 | Van Dijk et al. | 252/102 |

FOREIGN PATENT DOCUMENTS

| | | |
|---|---|---|
| 408131 | 1/1991 | European Pat. Off. . |
| 549271 | 6/1993 | European Pat. Off. . |
| 2054019 | 10/1971 | Germany . |

OTHER PUBLICATIONS

M. L. Tobe, "Base Hydrolysis of Transition–Metal Complexes", Adv. Inorg. Bioinorg. Mech. (1983), 2, pp. 1–94.

G. M. Williams et al., "Coordination Complexes of Cobalt", J. Chem. Ed. (1989), 66 (12), 1043–45.

W. L. Jolly, "The Synthesis and Characterization of Inorganic Compounds", (Prentice–Hall; 1970), pp. 461–463.

L. M. Jackman et al., "Synthesis of Transition–Metal Carboxylato Complexes", Inorg. Chem., 18, pp. 1497–1502 (1979).

T. J. Wierenga et al., "Synthesis and Characterization of Cobalt (III) Nicotinic Acid Complexes", Inorg. Chem., 21 (1982) pp. 2881–2885.

L. M. Jackman et al., "Reaction of Aquapentaamminecobalt(III) Perchlorate with Dicyclohexylcarbodiimide and Acetic Acid", Inorg. Chem., 18 (1979), pp. 2023–2025.

G. Schlessinger, "Carbonatotetramminecobalt(III) Nitrate", Inorg. Synthesis (1960) pp. 173–176.

F. Basolo et al., "Mechanism of Substitution Reactions in Complex Ions", Journal of Physical Chemistry, 56 (1952), PP. 22–25.

F. Basolo et al., "Acidopentamminecobalt(III) Salts", Inorg. Synthesis (1953), pp. 171–177.

Chan et al., "Octahedral Cobalt(III) Complexes and Reactions of the Chloropentakismethylaminecobalt(III) Cation", Anal. J. Chem., 1967, pp. 2229–2231.

Primary Examiner—Paul F. Shaver
Attorney, Agent, or Firm—K. W. Zerby; J. J. Yetter; J. C. Rasser

[57] ABSTRACT

A method for manufacturing cobalt complexes having the formula:

$$[Co(NH_3)_5OAc]T_y$$

said method comprising reacting cobalt (II) acetate having the formula $Co(OAc)_2 \cdot 4H_2O$ with concentrated ammonium hydroxide/ammonium acetate, followed by oxidizing agent (e.g., peroxide).

12 Claims, No Drawings

METHOD FOR MANUFACTURING COBALT CATALYSTS

TECHNICAL FIELD

The present invention relates to methods for manufacturing cobalt complexes having the formula:

$[Co(NH_3)_5M]T_y$.

wherein M ligand is selected from substituted and unsubstituted $C_1$–$C_{30}$ carboxylic acids having the formula:

$RC(O)O$—.

These catalysts are particularly useful in bleach-containing consumer compositions, especially automatic dishwashing detergents and laundry detergents comprising bleach.

BACKGROUND OF THE INVENTION

Cobalt catalysts are well known, as are a variety of methods for manufacturing them. Most synthesis methods, however, are directed simply to methods effective for obtaining experimental quantities for academic studies. These are described, for example, in M. L. Tobe, "Base Hydrolysis of Transition-Metal Complexes", *Adv. Inorg. Bioinorg. Mech.*, (1983), 2, pages 1–94; *J. Chem. Ed.* (1989), 66 (12), 1043–45; The Synthesis and Characterization of Inorganic Compounds, W. L. Jolly (Prentice-Hall; 1970), pp. 461–3; *Inorg. Chem.*, 18, 1497–1502 (1979); *Inorg. Chem.*, 21, 2881–2885 (1982); *Inorg. Chem.*, 18, 2023–2025 (1979); *Inorg. Synthesis*, 173–176 (1960); and *Journal of Physical Chemistry*, 56, 22–25 (1952).

For use in consumer products, however, it is necessary that the cobalt catalysts be prepared in large quantities by the most cost effective manner with the highest possible purity. It has been discovered by the present invention that cobalt catalysts containing carboxylate ligands can be prepared on an industrially useful scale by the present process.

BACKGROUND ART

U.S. Pat. No. 4,810,410, to Diakun et al, issued Mar. 7, 1989; U.S. Pat. No. 5,246,612, to Van Dijk et al., issued Sep. 21, 1993; U.S. Pat. No. 5,244,594, to Favre et al., issued Sep. 14, 1993; and European Patent Application, Publication No. 408,131, published Jan. 16, 1991 by Unilever NV, see also: U.S. Pat. No. 5,114,611, to Van Kralingen et al, issued May 19, 1992 (transition metal complex of a transition metal, such as cobalt, and a non-macro-cyclic ligand); U.S. Pat. No. 4,430,243, to Bragg, issued Feb. 7, 1984 (laundry bleaching compositions comprising catalytic heavy metal cations, including cobalt); German Patent Specification 2,054,019, published Oct. 7, 1971 by Unilever N.V. (cobalt chelant catalyst); and European Patent Application Publication No. 549,271, published Jun. 30, 1993 by Unilever PLC (macrocyclic organic ligands in cleaning compositions).

SUMMARY OF THE INVENTION

The present invention relates to methods for manufacturing cobalt complexes having the formula:

$[Co(NH_3)_5M]T_y$;

wherein the M ligand is selected from substituted and unsubstituted $C_1$–$C_{30}$ carboxylic acids having the formula:

$RC(O)O$—;

said method comprising the steps of:

(a) reacting cobalt (II) carboxylate (preferably acetate) having the formula:

$Co(M)_2 \cdot xH_2O$ wherein x is from about 0 to about 8, preferably from about 0 to about 6, more preferably from about 2 to about 4, with concentrated ammonium hydroxide and ammonium carboxylate salt (e.g., ammonium acetate);

(b) reacting the product of step (a) with an oxidizing agent selected from the group consisting of oxygen, hydrogen peroxide, and mixtures thereof;

(c) optionally, exchanging one T counterion with another T counterion; and (d) collecting the cobalt complex;

wherein T is one or more counteranions present in a number y to obtain a charge-balanced salt (preferred T are selected from the group consisting of chloride, iodide, $I_3^-$, formate, nitrate, nitrite, sulfate, sulfite, citrate, acetate, carbonate, bromide, $PF_6^-$, $BF_4^-$, $B(Ph)_4^-$, phosphate, phosphite, silicate, tosylate, methanesulfonate, and combinations thereof); and y is 1 or 2.

All parts, percentages and ratios used herein are expressed as percent weight unless otherwise specified. All documents cited are, in relevant part, incorporated herein by reference.

DETAILED DESCRIPTION OF THE INVENTION

The present invention relates to a method for manufacturing cobalt complexes having the formula:

$[Co(NH_3)_5M]T_y$.

The M ligand is selected from substituted and unsubstituted $C_1$–$C_{30}$ carboxylic acids having the formula:

$RC(O)O$—.

Herein, R is preferably selected from the group consisting of hydrogen and $C_1$–$C_{30}$ (preferably $C_1$–$C_{18}$) unsubstituted and substituted alkyl, $C_6$–$C_{30}$ (preferably $C_6$–$C_{18}$) unsubstituted and substituted aryl, and $C_3$–$C_{30}$ (preferably $C_5$–$C_{18}$) unsubstituted and substituted heteroaryl, wherein substituents are selected from the group consisting of —$NR'_3$, —$NR'_4^+$, —$C(O)OR'$, —$OR'$, —$C(O)NR'_2$, wherein R' is selected from the group consisting of hydrogen and $C_1$–$C_6$ moieties. Such substituted R therefore include the moieties —$(CH_2)_nOH$ and —$(CH_2)_nNR'_4^+$, wherein n is an integer from 1 to about 16, preferably from about 2 to about 10, and most preferably from about 2 to about 5.

Most preferred M are carboxylic acids having the formula above wherein R is selected from the group consisting of hydrogen, methyl, ethyl, propyl, straight or branched $C_4$–$C_{12}$ alkyl, and benzyl. Most preferred R is methyl. The M moieties include mono-carboxylates, which are preferred, but more than one carboxylate may be present in the moiety as long as the binding to the cobalt is by only one carboxylate per moiety (in which case the other carboxylate in the M moiety may be protonated or in its salt form). Preferred carboxylic acid M moieties include formic, benzoic, octanoic, nonanoic, decanoic, dodecanoic, malonic, maleic, succinic, adipic, phthalic, 2-ethylhexanoic, naphthenoic, oleic, palmitic, triflate, tartrate, stearic, butyric, citric, acrylic, aspartic, fumaric, lauric, linoleic, lactic, malic, and especially acetic acid.

T is one or more counteranions present in a number y to obtain a charge-balanced salt (preferred T are selected from the group consisting of chloride, iodide, $I_3^-$, formate, nitrate, nitrite, sulfate, sulfite, citrate, acetate, carbonate, bromide, $PF_6^-$, $BF_4^-$, $B(Ph)_4^-$, phosphate, phosphite, silicate, tosylate, methanesulfonate, and combinations thereof); and y is 1 or 2.

This method comprises the first step of reacting cobalt (II) carboxylate (preferably acetate) having the formula:

$$Co(M)_2 \cdot xH_2O$$

wherein M is a described hereinbefore, and x is from about 0 to about 8, preferably from about 0 to about 6, more preferably from about 2 to about 4, with concentrated ammonium hydroxide and ammonium carboxylate salt (preferably ammonium acetate; and preferably at least 20%, more preferably at least 25%, and typically between 28–32% solutions of concentrated ammonium hydroxide). This step is typically conducted at room temperature; preferred temperatures are below about 90° C., more preferably below 80° C. Preferred is to use from about 5.0 to about 10.0 equivalents, more preferably from about 5.0 to about 5.5 equivalents, of ammonium hydroxide in a concentrated aqueous solution so as to minimize the volume of water present during the reaction.

This first step is followed by a step whereby the product of the first step is reacted with an oxidizing agent selected from the group consisting of an oxidizing source such as oxygen and, especially, hydrogen peroxide (preferably at concentrations of at least about 30% and more preferably at least about 50% by weight). This step is also typically conducted at room temperature; preferred temperatures are below about 90° C., more preferably below 80° C.

This reaction step is then optionally followed by exchanging the T counterion of the prepared cobalt complex with another T counterion. This may be carried out, for example, by treating the complex with an acid (e.g., HCl or HClO_4), or a salt (e.g., NaPF_6).

At the end of the reaction process, the cobalt complex is collected. Preferred collection methods include, for example, evaporation to remove the solvent or lyophilization or precipitation (e.g., by addition of a co-solvent). The cobalt complex collected may be used as is, or further purified or modified for incorporation into the desired product or use to be made of the complex. This includes optionally washing the solid product with a suitable solvent, e.g., ethanol, to remove non-cobalt salts.

The present invention method preferably is carried out in one reaction vessel without isolation or separation of the intermediate reaction products. However, if desired, one or more of the reaction steps may be conducted in separate reaction vessels, and may be followed or preceeded by optional separation and/or collection steps of the intermediate reaction materials.

Preferred T are selected from the group consisting of chloride, iodide, $I_3^-$, formate, nitrate, nitrite, sulfate, sulfite, titrate, acetate, carbonate, bromide, $PF_6^-$, $BF_4^-$, $B(Ph)_4^-$, phosphate, phosphite, silicate, tosylate, methanesulfonate, and combinations thereof. Optionally, T can be protonated if more than one anionic group exists in T, e.g., $HPO_4^{2-}$, $HCO_3^-$, $H_2PO_4^-$, etc. Further, T may be selected from the group consisting of non-traditional inorganic anions such as anionic surfactants (e.g., linear alkylbenzene sulfonates (LAS), alkyl sulfates (AS), alkylethoxysulfonates (AES), etc.) and/or anionic polymers (e.g., polyacrylates, polymethacrylates, etc.).

The preferred cobalt complexes prepared by the present invention are cobalt(III) pentaamineacetate dichloride, i.e. $[Co(NH_3)_5OAc]Cl_2$; cobalt(III) pentaamineacetate diacetate, i.e. $[Co(NH_3)_5OAc](OAc)_2$ (herein "PAC"); $[Co(NH_3)_5OAc](PF_6)_2$; $[Co(NH_3)_5OAc](SO_4)$; and $[Co(NH_3)_5OAc](BF_4)_2$.

The starting cobalt (II) carboxylates useful herein are commercially available and can be prepared by a variety of methods.

The following nonlimiting examples further illustrate the method according to the present invention.

EXAMPLE 1

Synthesis of $[Co(NH_3)_5OAc](OAc)_2$ (designated as "PAC")

Ammonium hydroxide (286.0 mL, 2.06 mol, 28%) and ammonium acetate (68.81 g, 0.89 mol) are combined in a 1000 mL three-necked round-bottomed flask fitted with a condenser, internal thermometer, mechanical stirrer, and addition funnel. Once the mixture becomes homogeneous, cobalt(II) acetate tetrahydrate (100.00 g, 0.40 mol) is added in portions over 5 min. The mixture becomes black and warms to 31° C. The mixture is treated with $H_2O_2$ (27.32 g, 0.40 mol, 50%) dropwise over 15 min. The mixture further exotherms to 53° C. and turns deep red once addition is complete. After stirring for 1 h, HPLC analysis indicates that all of the cobalt is present as $[Co(NH_3)_5OAc](OAc)_2$. Concentration yields the desired complex as a red solid.

EXAMPLE 2

Synthesis of $[Co(NH_3)_5OAc](PF_6)_2$

The product of Example 1 is treated with 1 equivalent of $NaPF_6$ in water at room temperature. The reaction mixture is stirred for one 1 h, concentrated to a viscous liquid, and cooled to 10°–15° C. Red crystals precipitate from the mixture and are collected by filtration. HPLC analysis of the red product indicates all of the cobalt is present as $[Co(NH_3)_5OAc](PF_6)_2$.

What is claimed is:

1. A method for manufacturing cobalt complexes having the formula:

$$[Co(NH_3)_5M]T_y;$$

wherein the M ligand is selected from substituted and unsubstituted $C_1$–$C_{30}$ carboxylic acids having the formula:

$$RC(O)O—;$$

said method comprising the steps of:

(a) reacting cobalt (II) carboxylate having the formula:

$$Co(M)_2 \cdot xH_2O$$

wherein x is from about 0 to about 8, with concentrated ammonium hydroxide and ammonium carboxylate salt;

(b) reacting the product of step (a) with an oxidizing agent selected from the group consisting of oxygen, hydrogen peroxide, and mixtures thereof;

(c) optionally, exchanging one T counterion with another T counterion; and (d) collecting the cobalt complex;

wherein T is one or more counteranions present in a number y to obtain a charge-balanced salt; and y is 1 or 2.

2. The method according to claim 1 wherein T is selected from the group consisting of chloride, iodide, $I_3^-$, formate, nitrate, nitrite, sulfate, sulfite, citrate, acetate, carbonate, bromide, $PF_6^-$, $BF_4^-$, $B(Ph)_4^-$, phosphate, phosphite, silicate, tosylate, methanesulfonate, and combinations thereof.

3. The method according to claim 1 wherein the concentrated ammonium hydroxide is at least about 25% ammonium hydroxide.

4. The method according to claim 3 utilizing from about 5.0 to about 10.0 equivalents of ammonium hydroxide in a concentrated aqueous solution.

5. The method according to claim 1 wherein each R is independently selected from the group consisting of hydrogen and $C_1$–$C_{30}$ unsubstituted and substituted alkyl, $C_6$–$C_{30}$ unsubstituted and substituted aryl, and $C_3$–$C_{30}$ unsubstituted and substituted heteroaryl, wherein substituents are selected from the group consisting of —$NR'_3$, —$NR'_4{}^+$, —C(O)OR', —OR', —C(O)$NR'_2$, wherein R' is selected from the group consisting of hydrogen and $C_1$–$C_6$ moieties.

6. The method according to claim 5 wherein each R is independently selected from $C_1$–$C_{18}$ unsubstituted and substituted alkyl.

7. The method according to claim 6 wherein each R is independently selected from the group consisting of hydrogen, methyl, ethyl, propyl, straight or branched $C_4$–$C_{12}$ alkyl, and benzyl.

8. The method according to claim 7 wherein R is methyl.

9. The method according to claim 6 wherein each R is independently selected from the moieties —$(CH_2)_n OH$ and —$(CH_2)_n NR'_4{}^+$, wherein n is an integer from 1 to about 16.

10. The method according to claim 1 wherein the M ligand is a carboxylic acid moiety selected from formic, benzoic, octanoic, nonanoic, decanoic, dodecanoic, malonic, maleic, succinic, adipic, phthalic, 2-ethylhexanoic, naphthenoic, oleic, palmitic, triflate, tartrate, stearic, butyric, citric, acrylic, aspartic, fumaric, lauric, linoleic, lactic, malic, and acetic acid.

11. The method according to claim 10 wherein M is an acetic acid moiety.

12. The method according to claim 1 utilizing in step (a) from about 5.0 to about 10.0 equivalents of ammonium hydroxide in a concentrated aqueous solution and wherein the oxidizing agent of step (b) comprises hydrogen peroxide.

* * * * *